United States Patent

Mori et al.

[11] 3,953,496
[45] Apr. 27, 1976

[54] BIS(BENZAMIDO)-BENZOIC ACID DERIVATIVES

[75] Inventors: Takashi Mori, Tama; Sakae Takaku, Ageo; Yoshiyuki Osugi, Kodaira; Takashi Matsuno, Tokyo; Shogo Tomizawa, Tama, all of Japan

[73] Assignee: Chugai Seiyaku Kabushiki Kaisha, Tokyo, Japan

[22] Filed: Mar. 13, 1974

[21] Appl. No.: 451,003

[30] Foreign Application Priority Data
Mar. 27, 1973 Japan.............................. 48-34152
Feb. 20, 1974 Japan.............................. 49-19407

[52] U.S. Cl. .................. 260/471 R; 260/479 R; 260/519; 260/559 S; 424/230
[51] Int. Cl.² ..................................... C07C 103/78
[58] Field of Search............ 260/471 R, 479 R, 519, 260/559 S

[56] References Cited
OTHER PUBLICATIONS
Theilheimer, W., Synthetic Methods of Organic Chemistry, (Vol. 5)–1951, Pub. by S. Karger, N.Y., p. 217 relied on.

Theilheimer, W., Synthetic Methods of Organic Chemistry, (Vol. I.)–1942, Pub. by S. Karger, N.Y., p. 93 relied on.

*Primary Examiner*—James A. Patten
*Attorney, Agent, or Firm*—Browdy and Neimark

[57] ABSTRACT

A bis(benzamido)-benzoic acid derivative represented by the formula

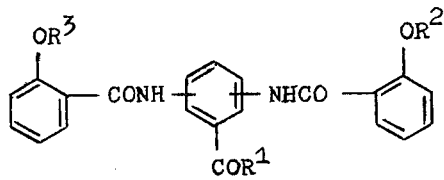

wherein $R^1$, $R^2$ and $R^3$ are as defined hereinbelow and a process for preparing the same is disclosed.

The compounds of the invention inhibit hemolysis of sheep red blood cell and cutaneous anaphylactic reaction, and also have an antipyretic sedative, anti-inflammatory and anti-allergic effect and are especially useful for treatment of rheumatic arthritis, bronchial asthma and nephritis.

28 Claims, No Drawings

BIS(BENZAMIDO)-BENZOIC ACID DERIVATIVES

This invention relates to a novel bis(benzamido)-benzoic acid derivative represented by the formula

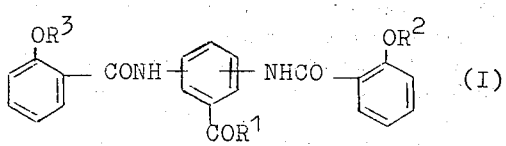

wherein $R^1$ is a hydroxyl radical, a lower alkoxy radical or an amino radical and $R^2$ and $R^3$ are independently a hydrogen atom, an acyl radical or a lower alkyl radical, and a process for preparing the same.

The compound represented by formula (I) according to this invention is prepared, for example, by reacting a compound of the formula

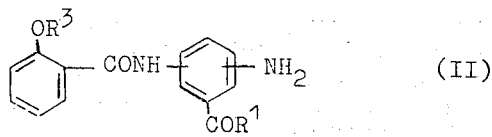

wherein $R^1$ and $R^3$ are as defined above, with a carboxylic acid represented by the formula

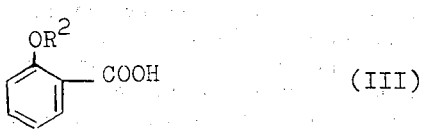

wherein $R^2$ is as defined above or a reactive derivative thereof, and if necessary, hydrolizing the ester radical or acylating one or two phenolic hydroxyl radicals of the compound (I).

The compound represented by formula (II) which is used as a starting compound may be readily prepared by condensing a nitroaminobenzoic acid with a carboxylic acid represented by the formula or a reactive derivative thereof

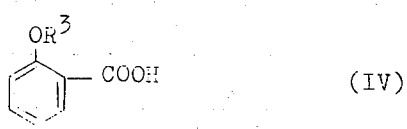

wherein $R^3$ is as defined above and then reducing the nitro radical of the compound in a conventional manner.

The examples of the compounds of the formulae (III) and (IV) and reactive derivatives thereof used in this invention include salicylic acid; 2-alkoxybenzoic acids wherein the number of carbon atoms of the alkyl moiety is between 1 to 4, for example, 2-methoxybenzoic acid, 2-ethoxybenzoic acid and 2-n-butoxybenzoic acid; 2-acyloxybenzoic acids wherein the number of carbon atoms of the acyl moiety is between 1 to 4, for example, 2-acetoxybenzoic acid; and corresponding acid halides, esters, acid anhydrides and acid anhydrides of the acid above with another acid, such as other carboxylic acid, carbonic acid, sulfuric acid, sulfonic acid, phosphoric acid and the like.

In an embodiment of this invention, the compound represented by formula (II) is subjected to condensation-reaction with the carboxylic acid of formula (III) or a reactive derivative thereof at a temperature ranging usually from −10° to 50°C, preferably from preferably, 0° to 20°C for a period of from 30 minutes to 4 hours. Solvents which may be used in the reaction include water, benzene, toluene, tetrahydrofuran, diethylether, dioxane, dimethylformamide, chloroform, methylene chloride, acetonitrile, acetone, carbon tetrachloride, ethyl acetate, a mixture thereof and the like.

Accelerators for the condensation-reaction include inorganic bases such as hydroxides, carbonates, and acetates of alkali metal or alkaline earth metal, for example, potassium acetate, sodium acetate, sodium carbonate, potassium carbonate, sodium hydroxide, calcium acetate and calcium carbonate; and tertiary amine organic base, for example, pyridine, triethylamine, dimethylaniline and picoline.

The compounds represented by formula (I) wherein $R^2$ and $R^3$ are identical are prepared also by reacting a compound represented by the formula

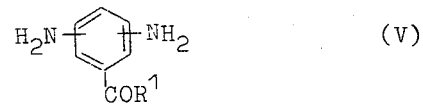

wherein $R^1$ is as defined above with a carboxylic acid represented by the formula

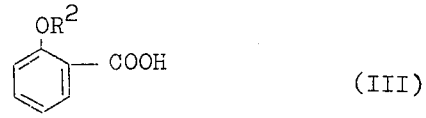

wherein $R^2$ is as defined above or a reactive derivative thereof, and optionally, hydrolizing the ester radical of the product or by acylating two phenolic hydroxy radicals of the product.

The compounds represented by formula (V) which can be used as a starting material include 3,5-diaminobenzoic acid, 3,4-diaminobenzoic acid, 2,4-diaminobenzoic acid, 2,5-diaminobenzoic acid, and alkyl esters of a diaminobenzoic acid (the number of carbon atoms of alkyl moiety being between 1 – 4), for example, methyl 2,4-diaminobenzoate, ethyl 2,4-diaminobenzoate, butyl 2,4-diaminobenzoate, methyl 3,5-diaminobenzoate, and 2,4-diaminobenzamide, 3,5-diaminobenzamide.

This reaction can be carried out by, for example, subjecting a compound represented by formula (V) to condensation-reaction with a reactive derivative of carboxylic acid represented by formula (III) at a temperature of from usually −10° to 50°C, preferably, 0° to 20°C for a period of from 30 minutes to 4 hours. Solvents which can be used in this reaction include, for example, water, benzene, toluene, tetrahydrofuran, diethyl ether, dioxane, dimethylformamide, chloroform, methylene chloride, acetonitrile, acetone, carbon tetrachloride, ethyl acetate, a mixture thereof and the like.

Accelerators which can be used in this reaction include, for example, inorganic bases such as hydroxide, carbonates and acetates of alkali metal or alkaline earth metal, for example, potassium acetate, sodium acetate, sodium carbonate, potassium carbonate, sodium hydroxide, calcium acetate and calcium carbonate; and tertiary amine organic bases, for example, pyridine, triethylamine, dimethylaniline and picoline.

In another aspect of this invention, a compound of formula (V) the amino radical of which was activated with the use of phosphorus trichloride or an ester of chlorophosphorous acid can be reacted with a compound represented by formula (III) at a temperature of from room temperature to reflux temperature of the solvent used. It is preferable to carry out this reaction after protecting the hydroxyl radical of the compound (V) wherein $R^1$ is hydroxyl. This reaction is carried out in the presence of a solvent, for example, a neutral solvent such as benzene, toluene, xylene, dioxane or tetrahydrofuran, or a basic solvent such as pyridine, triethylamine, dimethylaniline or picoline. If the reaction is carried out in the presence of a neutral solvent, it is preferable to use an accelerator of tertiary amine. The period required for the reaction is between 30 minutes and 3 hours.

In still another aspect of this invention, a compound of formula (V) can be reacted with a compound of formula (III) in an inert organic solvent in the presence of an accelerator for amide-formation, such as dicyclohexylcarbodiimide at a temperature of from room temperature to reflux temperature of a solvent used for 1 – 5 hours. In case the compound of formula (V) has a hydroxyl radical, it is preferred to have protected the radical prior to the reaction. Solvents which may be used in the reaction include benzene, toluene, tetrahydrofuran, chloroform, methylene chloride, acetonitrile and the like.

The compound of formula (I) thus formed may be hydrolized in the case of ester, or may be acylated in the case of the compound having one or two phenolic hydroxyl radicals. These reactions can be carried out in any conventional manner. For example, the hydrolysis of the ester can be accomplished by the action of a hydroxide or carbonate of alkali metal or alkaline earth metal in water or an aqueous organic solvent at a temperature of from room temperature to 100°C for 0.5 to 30 hours. The acylation of the phenolic hydroxyl radical can be carried out by the action of an acid chloride or acid anhydride of a lower fatty acid at 0° – 100°C for 1 – 10 hours. The use of solvent is not essential, but an inert solvent such as tetrahydrofuran, dioxane, or acetone may be used. A basic accelerator such as pyridine, triethylamine or sodium acetate or an acidic accelerator such as sulfuric acid or p-toluenesulfonic acid may be conveniently used.

In case the product has a free carboxyl radical, a pharmacologically acceptable salt thereof may be utilized for the same purpose as that of the product.

The compounds of the formula (I) according to this invention exhibit characteristic biological activities, especially upon a system concerning antigen-antibody reaction. For example, it is observed in in vitro tests that any of the water soluble compounds of formula (I) even in a very small amount can inhibit the hemolysis of sheep red blood cell (sRBC) which is induced by the reaction of sRBC and anti-sRBC mouse serum in the presence of complement (immune hemolysis). In animal tests, the compounds of the formula (I) highly inhibit cutaneous anaphylactic reaction by the oral administration even in a dose up to 100 mg/kg.

The compounds of formula (I) not only inhibit such immune reaction as stated above, but also have an anti-pyretic, sedative, anti-inflammatory and anti-allergic effect. The compounds are especially useful for treatment of diseases caused by immunological disorder, for example, rheumatic arthritis, bronchial asthma and nephritis.

The present invention will be further explained by way of the following experiments and examples. The invention, however, is not intended to be limited thereto.

EXPERIMENT 1

Activity inhibiting heat-induced hemolysis

Red blood cell (RBC) obtained from a Wister-Imamichi male rat were suspended in 0.15 M phosphate buffer (pH, 7.4) to obtain a 1% suspension of RBC. A test tube was charged with 5 ml of the suspension and then, 0.1 ml of 10% solution of dimethylsulfoxide in ethanol containing a compound to be tested was added to the suspension, followed by allowing it to incubate at 53°C for 20 minutes. The test tube was then cooled with water, and the content of the tube was centrifuged at 2,000 rpm for 10 minutes. Optical density of the supernatant thus obtained was measured with a Hitachi-124 spectrophotometer at 540 m$\mu$, and ratio of inhibiting hemolysis was estimated on the basis of the following equation.

Ratio of inhibiting hemolysis (%)

$$= \left(1 - \frac{\text{absorbance of incubated suspension containing testing compound} - \text{absorbance of non-incubated suspension containing no testing compound}}{\text{absorbance of incubated suspension not containing testing compound} - \text{absorbance of non-incubated suspension containing no testing compound}}\right) \times 100$$

The results are shown in the following Table 1.

Table 1

| Compounds | | Ratio of inhibiting hemolysis |
|---|---|---|
| Compound of | Example 1 | +++ |
| '' | Example 2 | +++ |
| '' | Example 3 | ++ |
| '' | Example 4 | ++ |
| '' | Example 5 | +++ |
| '' | Example 6 | +++ |
| '' | Example 7 | ++ |
| '' | Example 8 | +++ |
| '' | Example 9 | + |
| '' | Example 10 | ++ |
| '' | Example 11 | + |
| Compound of | Example 12 | + |
| '' | Example 13 | + |
| '' | Example 14 | ++ |
| '' | Example 17 | +++ |
| '' | Example 18 | +++ |
| '' | Example 19 | +++ |
| '' | Example 20 | + |
| '' | Example 32 | + |
| '' | Example 33 | ++ |
| Benzidamine | | + |
| Phenylbutazone | | − |
| Salicyclic acid | | − |
| Mefenamic acid | | + |

+++ : Above 80% inhibition at $1 \times 10^{-5}$M

Table 1-continued

| Compounds | Ratio of inhibiting hemolysis |
|---|---|
| +++ : | Around 50% inhibition at 1 × 10$^{-5}$M |
| ++ : | Below 20% inhibition at 1 × 10$^{-5}$M or Above 80% inhibition at 1 × 10$^{-4}$M |
| + : | Around 50% inhibition at 1 × 10$^{-4}$M |
| − : | Below 20% inhibition at 1 × 10$^{-4}$M |

EXPERIMENT 2

Inhibition of immune reaction-induced hemolysis
The following four solutions were prepared.

A. Antiserums solution

Commercially available sheep blood was washed three times with physiological salt solution and centrifuged at 2,000 rpm for 5 minutes. One ml of packed sRBC was resuspended in 10 ml of physiological salt solution. The resulting suspension was injected intravenously into mice (IV cs 5W) at a dose of 0.2 ml, and 4 days after the injection, a blood sample was obtained from the mice. From the sample, serum containing anti-sRBC antibody was recovered and diluted to 40 times its original volume with Vernal buffer solution having a pH of 7.5 containing gelatin, Ca$^{++}$ and Mg$^{++}$ (GVB$^{++}$) to obtain an anti-serum solution.

B. Complement solution

As a source of complement, guinea pig serum was employed. Guinea pig serum was diluted to 40 times its original volume with GVB$^{++}$ to obtain a solution of complement. All the procedures for preparing the solution were carried out under cooling.

C. sREC suspension sRBC was suspended in GVB$^{++}$. 0.25 ml of the suspension was completely homolyzed with water to fill up to 3.3 ml. Then, the resulting suspension was adjusted until optical density become 0.455 at 541 m$\mu$ upon completion of hemolysis.

D. Testing solution

A compound to be tested was dissolved in GVB$^{++}$ so as to obtain a concentration 1.5 times as high as that of the predetermined final concentration.

To 2 ml of the testing solution was added 0.5 ml of the anti-serum solution, 0.25 ml of sRBC suspension and 0.25 ml of the solution of complement, and the mixture was incubated at 37°C for 40 minutes. Then to the reaction mixture was added 0.3 ml of 3.8% aqueous trisodium citrate solution to terminate the reaction. sRBC not hemolyzed were separated off from the mixture by centrifuging for 5 minutes at 2,000 rpm. Absorbance of the supernatant was measured at 541 m$\mu$.

Separately, a control was prepared in the manner similar to that stated above, except that 2 ml of GVB$^{++}$ without testing compounds was used.

Incidentally, a blank solution was prepared in each assay by the procedure similar to that mentioned above, except that 0.25 ml of GVB$^{++}$ was used instead of 0.25 ml of the solution of complement, and errors of assay caused by the coloring of the testing solution were corrected.

Ratio of inhibiting hemolysis (%) was estimated in accordance with the following equation.

Ratio of inhibiting hemolysis (%)
$$= \left(1 - \frac{\text{absorbance of sample containing testing compound} - \text{absorbance of corresponding blank}}{\text{absorbance of the control} - \text{absorbance of the blank of control}}\right) \times 100$$

The results obtained are shown in the following Table 2.

Table 2

| Compounds | Ratio of inhibiting hemolysis |
|---|---|
| Compound of Example 1 | +++ |
| ″ Example 2 | +++ |
| ″ Example 8 | +++ |
| Mefenamic acid | + |
| Disodium chromoglycate | + |
| Salicyclic acid | − |
| Phenylbutazone | ++ |

| | |
|---|---|
| +++ : | Above 50% inhibition at 3.5 × 10$^{-4}$M or Above 80% inhibition at 8.8 + 10$^{-4}$M |
| ++ : | 50 – 80% inhibition at 8.8 × 10$^{-4}$M |
| + : | 20 – 50% inhibition at 8.8 × 10$^{-4}$M |
| − : | Below 20% inhibition at 8.8 × 10$^{-4}$M |

EXAMPLE 1

A solution of 17.5 g of 2-acetoxybenzoylchloride in 20 ml of dioxane was added at one time to a mixture of 4.6 g of 3,5-diaminobenzoic acid, 15.3 g of potassium acetate and 80 ml of water while stirring at a temperature of from 0° to 5°C. The stirring was continued at that temperature for one hour, then at room temperature for 30 minutes and at 50°C for 30 minutes. The resulting reaction mixture was added to 200 ml of cold diluted hydrochloric acid and the undissolved substance was separated. The substance was dissolved in about 100 ml of 1N NaOH aqueous solution and then the solution was treated with active carbon and acidified with hydrochloric acid so as to bring the pH of the solution to 3 – 4 thereby precipitating crystals. The crystals were recovered by filtration and washed with water. Recrystallization from methanol-water gave 7.2 g of 3,5-bis(salicylamido)-benzoic acid having a melting point between 305° – 108°308°(decomposition).

Analysis: Calcd.: C, 64.3; H, 4.1; N, 7.1 (%); Found: C, 64.5; H, 4.1; N, 7.1 (%).

EXAMPLE 2

A solution of 17.2 g of 2-acetoxybenzoylchloride in 20 ml of dioxane was added at one time to a mixture of 4.6 g of 3,4-diaminobenzoic acid, 15.3 g of potassium acetate and 70 ml of water while stirring at a temperature of from 0° to 5°C, followed by stirring at that temperature for 30 minutes. To the mixture was added a solution of 1 g of 2-acetoxybenzoylchloride in 3 ml of dioxane. The resulting mixture was stirred at room temperature for 30 minutes and then at 50°C for 30 minutes. The reaction mixture was added to 200 ml of cold diluted hydrochloric acid and the undissolved mixture of oil and powdery solid was separated. The mixture was dissolved in about 100 ml of 1N aqueous sodium hydroxide solution, and the solution was treated with active carbon and then acidified to precipitate crystals. The crystals were recovered by filtration and washed with water. Recrystallization from a mixture of dioxane and water gave 6.9 g of 3,4-bis(salicylamido)-benzoic acid having a melting point between 305° – 307°C (decomposition).

Analysis: Calcd.: C, 64.3; H, 4.1; N, 7.1 (%); Found: C, 64.4; H, 4.1; N, 6.8 (%).

EXAMPLE 3

A mixture of 3.32 g of methyl 2,5-diaminobenzoate, 5.8 ml of triethylamine and 20 ml of tetrahydrofuran was added dropwise to a solution of 8.7 g of 2-acetoxybenzoylchloride in 150 ml of tetrahydrofuran over 30 minutes, while stirring at 5° – 10°C. After completion of the addition, the reaction mixture was stirred at room temperature for 1 hour and then poured into 500 ml of ice-water to precipitate crystals. The crystals were recovered by filtration, washed with water and dried in air. Recrystallization from ethyl acetate gave 8.1 g of methyl 2,5-bis(2'-acetoxybenzamido)-benzoate having a melting point between 170° – 171°C.

Analysis: Calcd.: C, 63.7; H, 4.5; N, 5.7 (%); Found: C, 63.5; H, 4.6; N, 5.7 (%).

EXAMPLE 4

In 150 ml methanol was dissolved 5.3 g of methyl 2,5-bis(2'-acetoxybenzamido)-benzoate obtained in Example 3. To the solution was added 2.5 g of sodium carbonate dissolved in 40 ml of water and then the mixture was stirred at room temperature for 30 minutes. The mixture was poured into 500 ml of water containing 10 ml of acetic acid to precipitate crystals. The crystals were recovered by filtration, washed with water, dried and recrystallized from ethyl acetate to yield 3.8 g of methyl 2,5-bis(salicylamido)-benzoate having a melting point between 243° – 244°C.

Analysis: Calcd.: C, 65.0 H, 4.5; N, 6.9 (%); Found: C, 65.1; H, 4.6; N, 7.0 (%).

EXAMPLE 5

An aqueous solution of 4 g of sodium hydroxide in 10 ml of water was added to a mixture of 5.3 g of methyl 2,5-bis(2'-acetoxybenzamido)-benzoate obtained in Example 3 and 100 ml of methanol. The resulting mixture was stirred at room temperature for 20 – 30 hours and then poured into 500 ml of water containing 10 ml of acetic acid to precipitate crystals. The crystals were recovered by filtration, washed with water and recrystallized from a mixture of dioxane and water to yield 3.5 g of 2,5-bis(salicylamido)-benzoic acid having a melting point between 280° – 283°C (decomposition).

Analysis: Calcd.: C, 64.3; H, 4.1; N, 7.1 (%); Found: C, 64.3; H, 4.0; N, 6.9 (%).

EXAMPLE 6

A mixture of 6.64 g of methyl 2,4-diaminobenzoate, 11.5 ml of triethylamine and 50 ml of tetrahydrofuran was added dropwise to a solution of 17.4 g of 2-acetoxybenzoylchloride in 300 ml of tetrahydrofuran over 0.5 – 1 hour, while stirring at 5° – 10°C. The stirring was then continued at room temperature for 2 hours. The resulting reaction mixture was poured into 1.5 $l$ of diluted hydrochloric acid to precipitate crystals. The crystals were recovered by filtration, washed with water, dried and recrystallized from ethyl acetate to yield 15 g of methyl 2,4-bis(2'-acetoxybenzamido)-benzoate having a melting point between 143° – 145°C.

Analysis: Calcd.: C, 63.7; H, 4.5; N, 5.7 (%); Found: C, 63.5; H, 4.3; N, 5.6 (%).

EXAMPLE 7

By the procedure similar to that described in Example 4, methyl 2,4-bis(2'-acetoxybenzamido)-benzoate was hydrolized with the aid of sodium carbonate to obtain crystals. Recrystallization of the crystals from a mixture of acetone, dioxane and water gave methyl 2,4-bis(salicylamido)-benzoate having a melting point between 259° – 260°C. (Yield: 82%)

Analysis: Calcd.: C, 65.0; H, 4.5; N, 6.9 (%); Found: C, 65.1; H, 4.4; N, 6.8 (%).

EXAMPLE 8

By the procedure similar to that described in Example 5, methyl 2,4-bis(2'-acetoxybenzamido)-benzoate obtained in Example 6 was hydrolized with the aid of sodium hydroxide. Recrystallization of the hydrolized product from a mixture of dioxane and water gave 2,4-bis(salicylamido)-benzoic acid having a melting point between 250° – 252°C (decomposition). (Yield; 85%)

Analysis: Calcd.: C, 64.3; H, 4.1; N, 7.1 (%); Found; C, 64.1; H, 4.2; N, 6.9 (%).

EXAMPLE 9

A solution of 3.86 ml of phosphorus oxychloride in 20 ml of tetrahydrofuran was added dropwise to a mixture of 3.3 g of methyl 2,4-diaminobenzoate, 6.7 g of 2-methoxybenzoic acid, 1.8 ml of triethylamine and 100 ml of tetrahydrofuran over 1 – 2 hours while stirring at −10° to −5°C, followed by stirring at room temperature for one hour. The reaction mixture was then poured into 1 $l$ of icewater to precipitate crystals. The crystals were recovered by filtration, washed with water, dried and recrystallized from ethyl acetate to obtain 7.2 g of methyl 2,4-bis(2'-methoxybenzamido)-benzoate having a melting point between 166° – 167°C.

Analysis: Calcd.: C, 66.4; H, 5.1; N, 6.5 (%); Found: C, 66.6; H, 5.1; N, 6.5 (%).

EXAMPLE 10

5 g of methyl 2,4-bis(2'-methoxybenzamido)-benzoate obtained in Example 9 was admixed with 250 ml of dioxane, 3 g of potassium hydroxide and 50 ml of water, followed by stirring the mixture at room temperature for 20 to 30 hours. The mixture was then poured into 1.5 $l$ of ice-water containing 20 ml of acetic acid to precipitate crystals. The crystals were recovered by filtration, washed with water and recrystallized from ethanol-water to yield 3.6 g of 2,4-bis(2'-methoxybenzamido)-benzoic acid having a melting point between 232° – 233°C.

Analsysis: Calcd.: C, 65.7; H, 4.8; N, 6.7 (%); Found: C, 65.4; H, 4.9; N, 6.7 (%).

EXAMPLE 11

In 250 ml of tetrahydrofuran was dissolved 2 g of 2,4-diaminobenzamide and 3.7 ml of triethylamine, and to the solution was added dropwise a solution of 4.5 g of 2-methoxybenzoylchloride in 20 ml of tetrahydrofuran over one hour, followed by stirring at room temperature for one hour. The reaction mixture was then poured into 1.5 $l$ of diluted hydrochloric acid to precipitate crystals. The crystals were recovered by filtration, washed with water and recrystallized from a mixture of dimethylformamide and water to obtain 4.1 g of 2,4-bis(2'-methoxybenzamido)-benzamide having a melting point between 270° – 272°C (decomposition).

Analysis: Calcd.: C, 65.9; H, 5.1; N, 10.0 (%); Found: C, 65.7; H, 5.3; N, 10.1 (%).

EXAMPLE 12

In 40 ml of tetrahydrofuran was dissolved 4.35 g of 2-acetoxybenzoylchloride, and to the solution was added 1.5 g of 3,5-diaminobenzamide. A soluton of 3.08 ml of triethylamine in 10 ml of tetrahydrofuran was added dropwise to the reaction mixture over 1.5 hours while stirring at room temperature, followed by stirring at room temperature for two hours. The reaction mixture thus obtained was then poured into 300 ml of cold diluted hydrochloric acid and extracted with ethyl acetate. The organic layer was washed with water, dried over sodium sulfate and concentrated under reduced pressure. Recrystallization of the residue from hot benzene gave 2.1 g of 3,5-bis(2'-acetoxybenzamido)-benzamide having a melting point at above 105°C (decomposition).

Analysis: Calcd.: C, 63.2; H, 4.5; N, 8.8 (%); Found: C, 63.0; H, 4.4; N, 8.6 (%).

EXAMPLE 13

In the manner similar to that described in Example 4, 3,5-bis(2'-acetoxybenzamido)-benzamide obtained in Example 12 was hydrolyzed with sodium carbonate. Recrystallization of the hydrolized product from a mixture of ethanol and water gave 3,5-bis(salicylamido)-benzamide having a melting point between 276° – 277°C. (Yield; 83%)

Analysis: Calcd.: C, 64.4; H, 4.4; N, 10.7 (%); Found: C, 64.1; H, 4.7; N, 10.7 (%).

EXAMPLE 14

A solution of 16.2 g of 2-methoxybenzoylchloride in 40 ml of dioxane was added dropwise to a mixture of 4.6 g of 3,5-diaminobenzoic acid, 15.3 g of potassium acetate and 70 ml of water over 30 minutes while stirring at 0° – 5°C, followed by stirring at room temperature for one hour and then at 50°C for another one hour. The reaction mixture was cooled and poured into 100 ml of diluted hydrochloric acid to precipitate crystals. The crystals were recovered by filtration, washed with water and recrystallized from ethanol to yield 6 g of 3,5-bis(2'-methoxybenzamido)-benzoic acid having a melting point between 253° – 254°C.

Analysis: Calcd.: C, 65.7; H, 4.8; N, 6.7 (%); Found: C, 65.5; H, 4.9; N, 6.5 (%).

EXAMPLE 15

In 200 ml of pyridine was dissolved 8.3 g of methyl 2,4-diaminobenzoate, and to the solution was added a solution of 4.4 ml of phosphorus trichloride in 30 ml of pyridine under cooling with ice, followed by stirring at 50° to 70°C for one hour. To the mixture was added 21 g of salicylic acid was added, followed by heating at 90°C for three hours. After the cooling of the mixture by allowing it to stand, undissolved substances were filtered off and the filtrate was subjected to concentrate under reduced pressure. The concentrate was added to cold diluted hydrochloric acid to precipitate crystals. The crystals were recovered by filtration, washed with water and recrystallized from an acetone-dioxane-water mixture to obtain 11.1 g of methyl 2,4-bis(-salicylamido)-benzoate having a melting point between 259° – 260°C. It was confirmed that the product was identical to that obtained in Example 7.

EXAMPLE 16

By the procedure similar to that described in Example 15, methyl 2,5-diaminobenzoate was condensed with salicylic acid with the aid of phosphorus trichloride to obtain methyl 2,5-bis(salicylamido)-benzoate (Yield; 54%). The product was confirmed to be identical to that obtained in Example 4.

EXAMPLE 17

One g of 3,5-bis(salicylamido)-benzoic acid obtained in Example 1 was mixed with 30 ml of acetic anhydride and 3 ml of pyridine, followed by stirring the mixture at room temperature for 3 hours. Into the reaction mixture was poured 100 ml of ice-water to precipitate crystals which were recovered by filtration. Recrystallization from a dioxane-water mixture gave 0.8 g of 3,5-bis(2'-acetoxybenzamido)-benzoic acid having a melting point between 211° – 212°C (decomposition).

Analysis: Calcd.: C, 63.0; H, 4.2; N, Found: (%); Found C, 62.8; H, 4.4; N, 5.7 (%).

EXAMPLE 18

To a mixture of 4.9 g of 2,4-diaminobenzoic acid, 12 g of sodium acetate, 90 ml of methylene chloride and 90 ml of water was added 19.2 g of 2-acetoxybenzoylchloride while stirring at 5° – 10°C, followed by continuing the stirring at 5° – 15°C for 4 hours. The precipitated crystals were recovered by filtration, washed with water and then with methylene chloride and thoroughly mixed with 70 ml of methanol. To the mixture was added 30 ml of water, followed by allowing to stand to precipitate crystals. The crystals were recovered by filtration and recrystallized from 90% aqueous methanol to obtain 7.5 g of 2,4-bis(2'-acetoxybenzamido)-benzoic acid having a melting point between 194° – 195°C.

Analysis: Calcd.: C, 63.0; H, 4.2; N, 5.9 (%); Found: C, 62.7; H, 4.1; N, 6.0 (%).

EXAMPLE 19

By the procedure similar to that described in Example 1, 2,4-diaminobenzoic acid was condensed with 2-ethoxybenzoylchloride to obtain 2,4-bis(2'-ethoxybenzamido)-benzoic acid having a melting point between 225° – 226°C.

Analysis: Calcd.: C, 67.0% H, 5.4; N, 6.3 (%); Found: C, 66.7; H, 5.5; N, 6.0 (%).

EXAMPLE 20

By the procedure similar to that described in Example 12, 3,5-diaminobenzamide was condensed with 2-methoxybenzoylchloride to obtain 3,5-bis(2'-methoxybenzamido)-benzamide having a melting point between 226° – 227°C.

Analysis: Calcd.: C, 65.9; H, 5.1; N, 10.0 (%); Found: C, 65.5; H, 5.3; N, 10.1 (%).

EXAMPLE 21

In 80 ml of tetrahydrofuran were dissolved 2 g of methyl 2-(2'-acetoxybenzamido)-4-aminobenzoate and 11.8 g of 2-acetoxybenzoylchloride, and to the solution was added dropwise a solution of 0.6 g of triethylamine in 5 ml of tetrahydrofuran while stirring under cooling with ice. Ten minutes after completion of the addition, the mixture was returned to room temperature, followed by stirring at that temperature for one hour. The reaction mixture was then poured into diluted hydrochloric acid-ice to precipitate crystals. The crystals were recovered by filtration and recrystallized from methanol to obtain 2.0 g of methyl 2,4-bis(-2'-acetoxybenzamido)-benzoate having a melting point between 143° – 145°C. This product was confirmed to be identical to that obtained in Example 6.

EXAMPLE 22

By the procedure similar to that described in Example 21, ethyl 2-(2''-acetoxybenzamido)-4-aminobenzoate and 2-acetoxybenzoylchloride were treated to obtain crystals. Recrystallization from ethyl acetate gave ethyl 2,4-bis(2'-acetoxybenzamido)-benzoate having a melting point between 154° – 155°C.

Analysis: Calcd. for $C_{27}H_{24}N_2O_8$: C, 64.3; H, 4.8; N, 5.6 (%); Found: C, 64.4; H, 4.9; N, 5.5 (%).

EXAMPLE 23

In 10 ml of dioxane was dissolved 0.5 g of 2-(2'-methoxybenzamido)4aminobenzoic acid, and to the resulting solution was added a solution of 0.38 of sodium acetate trihydrate in 10 ml of water. To the mixture was added a solution of 0.37 g of 2-acetoxybenzoylchloride in 8 ml of dioxane, while stirring under cooling with ice. Ten minutes after completion of the addition, the mixture was allowed to return to room temperature, followed by stirring at that temperature for 2 hours. The mixture was then poured into diluted hydrochloric acid-ice to obtain crystals. Recrystallization from water-ethanol gave 0.55 g of 2-(2'-methoxybenzamido-4-(2'-acetoxybenzamido)-benzoic acid having a melting point between 203° – 204°C.

Analysis: Calcd. for $C_{24}H_{20}N_2O_7$: C, 64.3; H, 4.5; N, 6.3 (%); Found: C, 64.3; H, 4.4; N, 6.3 (%).

EXAMPLE 24

By the procedure similar to that described in Example 23, 2-(2'-acetoxybenzamido)-4-aminobenzoic acid and 2-acetoxybenzoylchloride were allowed to react and were treated to obtain crude crystals. Recrystallization from methanol-water gave 2,4-bis(2'-acetoxybenzamido)-benzoic acid having a melting point between 194° – 195°C. The product wass confirmed to be identical to that obtained in Example 18.

EXAMPLE 25

To a mixture of 70 ml of methanol and 50 ml of 10% aqueous sodium hydroxide, was added 0.45 g of 2-(2'-methoxybenzamido)-4-(2'-acetoxybenzamido)-benzoic acid, followed by stirring at room temperature for 2 hours. The mixture was poured into diluted hydrochloric acid-ice to obtain 0.39 g of crystals. Recrystallization from tetrahydrofuran-methanol gave 2-(2'-methoxybenzamido)-4-(salicylamido)-benzoic acid having a melting point between 253° – 254°C.

Analysis: Calcd. for $C_{22}H_{18}N_2O_6$: C, 65.0; H, 4.5; N, 6.9 (%); Found: C, 64.8; H, 4.4; N, 6.7 (%).

EXAMPLE 26

By the procedure similar to that described in Example 23, 2-(2'-acetoxybenzamido)-4-aminobenzoic acid and 2-methoxybenzoylchloride were allowed to react and were treated to obtain crude crystals. Recrystallization from ethanol gave 2-(2'-acetoxybenzamido)-4-(2'-methoxybenzamido)-benzoic acid having a melting point between 197° – 198°C.

Analysis: Calcd. for $C_{24}H_{20}N_2O_7$: C, 64.3; H, 4.5; N, 6.3 (%); Found: C, 63.9; H, 4.5; N, 6.2 (%).

EXAMPLE 27

A mixture of 0.4 g of 2-(2'-acetoxybenzamido-4-(2'-methoxybenzamido)-benzoic acid obtained in Example 26, 100 ml of methanol, and 30 ml of 28% aqueous ammonia was stirred at room temperature for 2 hours, and poured into diluted hydrochloric acid-ice to give 3 g of crystals which precipitated. Recrystallization from tetrahydrofuranmethanol gave 2-salicylamido-4-(2'-methoxybenzamido)-benzoic acid having a melting point between 263° – 264°C.

Analysis: Calcd. for $C_{22}H_{18}N_2O_6$: C, 65.0; H, 4.5; N, 6.9 (%); Found: C, 64.7; H, 4.4; N, 6.7 (%).

EXAMPLE 28

In 10 ml of dioxane was dissolved 0.6 g of 2-salicylamido-4-aminobenzoic acid and to the solution was added a solution of 0.35 g of sodium acetate in 10 ml of water, followed by adding a solution of 0.56 g of 2-acetoxybenzoylchloride in 10 ml of dioxane while stirring under cooling with ice. Ten minutes after completion of the addition, the mixture was allowed to return to room temperature and then stirred at that temperature for 2 hours. The reaction mixture was poured into diluted hydrochloric acid-ice to obtain 0.7 g of crystals which precipitated. Recrystallization from ethanol gave 2-salicylamido-4-(2'-acetoxybenzamido)-benzoic acid decomposing between 227° – 228°C.

Analysis: Calcd. for $C_{23}H_{18}N_2O_7$: C, 63.6; H, 4.2; N, 6.5 (%); Found: C, 63.3; H, 4.5; N, 6.2 (%).

EXAMPLE 29

In 6 ml of dimethylformamide was dissolved 0.54 g of 2-salicylamido-4-aminobenzoic acid, and to the solution was added 0.4 g of triethylamine and, also, dropwise, a solution of 0.62 g of salicylchloride in 5 ml of tetrahydrofuran while stirring under cooling with ice. Thirty minutes after completion of the addition, the mixture was allowed to return to room temperature followed by stirring at that temperature for 2 hours. The mixture was then poured into ice-water to obtain crystals which precipitated. The crude crystals thus obtained were dissolved in tetrahydrofuran. The solution was alkalified with sodium hydroxide, followed by stirring at room temperature for 30 minutes, and then poured into diluted hydrochloric acid-ice. Recrystallization of 0.4 g of the crude crystals from dimethylformamide-water to obtain the product which was identical to that obtained in Example 8.

EXAMPLE 30

By the procedure similar to that described in Example 23, 2-(2'-methoxybenzamido)-4-aminobenzoic acid and 2-methoxybenzoylchloride were reacted and treated to obtain crude crystals. Recrystallization from aqueous alcohol gave 2,4-bis(2'-methoxybenzamido)-benzoic acid having a melting point between 232° – 233°C which was identical to that obtained in Example 10.

EXAMPLE 31

By the procedure similar to that described in example 21, ethyl 2-(2'-n-butoxybenzamido)-4-aminobenzoate and 2-n-butoxybenzoylchloride were reacted and treated to obtain crude crystals. Recrystallization from ethanol gave ethyl 2,4-bis(2'-n-butoxybenzamido)-benzoate having a melting point between 134° – 136°C.

Analysis: Calcd. for $C_{29}H_{32}N_2O_6$: C, 69.9; H, 6.8; N, 5.3 (%); Found: C, 70.0; H, 6.8; N, 5.3 (%).

EXAMPLE 32

By the procedure similar to that described in Example 21, n-butyl 2-(2'-acetoxybenzamido)-4-aminobenzoate and 2'-acetoxybenzoylchloride were reacted and treated to obtain a sticky mass. The mass was dissolved in diethyl ether and a physical stimulus was given to the solution to obtain crystals which precipitated. Recrystallization from ethanol gave n-butyl 2,4-bis(2'-acetoxybenzamido)-benzoate having a melting point between 149° – 152°C.

Analysis: Calcd. for $C_{29}H_{28}N_2O_8$: C, 65.4; H, 5.3; N, 5.3 (%); Found: C, 65.7 H, 5.2; N, 5.3 (%).

EXAMPLE 33

By the procedure similar to that described in Example 23, 2-amino-4-(2'-acetoxybenzamido)-benzoic acid and 2-methoxybenzoylchloride were reacted and treated to obtain crude crystals. Recrystallization from water-ethanol gave 2-(2'-methoxybenzamido)-4-(2'-acetoxybenzamido)-benzoic acid which was identical to that of Example 23.

EXAMPLE 34

By the procedure similar to that described in Example 21, methyl 2-amino-4-(2'-ethoxybenzamido)-benzoate and 2-ethoxybenzoylchloride were reacted and treated to obtain crystals. Recrystallization from acetone gave methyl 2,4-bis(2'-ethoxybenzamido)-benzoate having a melting point between 199° – 200°C.

Analysis: Calcd. for $C_{26}H_{26}N_2O_6$: C, 67.5; H, 5.7; N, 6.1 (%); Found: C, 67.5; H, 5.5; N, 6.0 (%).

What is claimed is:

1. A bis(benzamido)-benzoic acid derivative represented by the formula

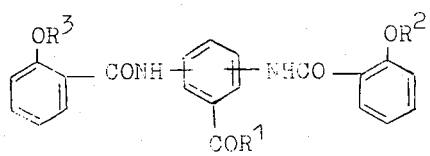

wherein $R^1$ is a hydroxyl radical, a lower alkoxy radical or an amino radical and $R^2$ and $R^3$ are same or different and each represents a hydrogen atom, a lower alkanoyl radical or a lower alkyl radical.

2. 3,5Bis(salicylamido)-benzoic acid in accordance with claim 1.

3. 3,4-Bis(salicylamid)-benzoic acid in accordance with claim 1.

4. Methyl 2,5-bis(-2'-acetoxybenzamido)-benzoate in accordance with claim 1.

5. Methyl 2,5-bis(salicylamido)-benzoate in accordance with claim 1.

6. 2,5-Bis(salicylamido)-benzoic acid in accordance with claim 1.

7. Methyl 2,4-bis(2'-acetoxybenzamido)-benzoate in accordance with claim 1.

8. Methyl 2,4-bis(salicylamido)-benzoate in accordance with claim 1.

9. 2,4-bis(salicylamido)-benzoic acid in accordance with claim 1.

10. Methyl 2,4-bis(2'-methoxybenamido)-benzoate in accordance with claim 1.

11. 2,4-Bis(2'-methoxybenzamido)-benzoic acid in accordance with claim 1.

12. 2,4-Bis(2'-methoxybenzamido)-benzamide in accordance with claim 1.

13. 3,5-Bis(2'-acetoxybenzamido)-benzamide in accordance with claim 1.

14. 3,5-Bis(salicylamido)-benzamide in accordance with claim 1.

15. 3,5-Bis(2'-methoxybenzamido)-benzoic acid in accordance with claim 1.

16. 3,5-Bis(2'-acetoxybenzamido)-benzoic acid in accordance with claim 1.

17. 2,4-Bis(2'-acetoxybenzamido)-benzoic acid in accordance with claim 1.

18. 2,4-Bis(2'-ethoxybenzamido)-benzoic acid in accordance with claim 1.

19. 3,5-Bis(2'-methoxybenzamido)-benzamide in accordance with claim 1.

20. Ethyl 2,4-bis(2'-acetoxybenzamido)-benzoate in accordance with claim 1.

21. 2-(2'-Methoxybenzamido)-4-(2'-acetoxybenzamido)-benzoic acid in accordance with claim 1.

22. 2-(2'-Methoxybenzamido)-4-(salicylamido)-benzoic acid in accordance with claim 1.

23. 2-2'-Acetoxybenzamido)-4-(2'-methoxybenzamido)-benzoic acid in accordance with claim 1.

24. 2-Salicylamido-4-2'-methoxybenzamido)-benzoic acid in accordance with claim 1.

25. 2-Salicylamido-4-(2'-acetoxybenzamido)-benzoic acid in accordance with claim 1.

26. Ethyl 2,4-bis(2'-n-butoxybenzamido)-benzoate in accordance with claim 1.

27. n-Butyl 2,4-bis(2'-acetoxybenzamido)-benzoate in accordance with claim 1.

28. Methyl 2,4-bis(2'-ethoxybenzamido)-benzoate in accordance with claim 1.

* * * * *

UNITED STATES PATENT AND TRADEMARK OFFICE
CERTIFICATE OF CORRECTION

PATENT NO. : 3,953,496
DATED : April 27, 1976
INVENTOR(S) : Takashi Mori et al

It is certified that error appears in the above-identified patent and that said Letters Patent are hereby corrected as shown below:

Column 2, lines 5-6 delete "preferably" second occurrence

Column 4, Table 1, Compound of Example 6    +++
                     Compound of Example 17   +++
                     Compound of Example 18   +++

Column 5, delete first three lines

Column 6, lines 14-15:

+++ : $\begin{cases} \text{Above 50\% inhibition at } 3.5 \times 10^{-4}\text{M or} \\ \text{Above 80\% inhibition at } 8.8 \times 10^{-4}\text{M} \end{cases}$ ++ :   50-80% inhibition at $8.8 \times 10^{-4}$M + :   20-50% inhibition at $8.8 \times 10^{-4}$M Column 6, line 41, delete "108°"

Column 10, line 20, delete "Found:" and insert --5.9--

Signed and Sealed this

Twenty-sixth Day of October 1976

[SEAL]

Attest:

RUTH C. MASON
*Attesting Officer*

C. MARSHALL DANN
*Commissioner of Patents and Trademarks*